US010161180B2

(12) United States Patent
Carme

(10) Patent No.: US 10,161,180 B2
(45) Date of Patent: Dec. 25, 2018

(54) MULTI-GLAZED WINDOW INCORPORATING AN ACTIVE NOISE REDUCTION DEVICE

(71) Applicants: TECHNOFIRST, Aubagne (FR); Christian Carme, Marseilles (FR)

(72) Inventor: Christian Carme, Marseilles (FR)

( * ) Notice: Subject to any disclaimer, the term of this patent is extended or adjusted under 35 U.S.C. 154(b) by 0 days.

(21) Appl. No.: 15/772,891

(22) PCT Filed: Nov. 2, 2016

(86) PCT No.: PCT/FR2016/052837
§ 371 (c)(1),
(2) Date: May 2, 2018

(87) PCT Pub. No.: WO2017/077234
PCT Pub. Date: May 11, 2017

(65) Prior Publication Data
US 2018/0313138 A1 Nov. 1, 2018

(30) Foreign Application Priority Data
Nov. 2, 2015 (FR) .................................... 15 60492

(51) Int. Cl.
*A61F 11/06* (2006.01)
*G10K 11/16* (2006.01)
(Continued)

(52) U.S. Cl.
CPC ...... *E06B 3/6707* (2013.01); *G10K 11/17857* (2018.01); *H04R 1/08* (2013.01);
(Continued)

(58) Field of Classification Search
CPC .... E06B 3/6707; G10K 11/17857; H04R 1/08
See application file for complete search history.

(56) References Cited

U.S. PATENT DOCUMENTS 6,285,773 B1 * 9/2001 Carme .................... H04R 9/06 181/150
2015/0086048 A1 * 3/2015 Brown .................... H04R 1/02 381/152

FOREIGN PATENT DOCUMENTS

CN 201 620 733 U 11/2010
EP 0 710 946 A1 5/1996
JP 2006-215510 A 8/2006

OTHER PUBLICATIONS

Written Opinion of the International Search Authority dated Feb. 16, 2017 of corresponding corresponding International application No. PCT/FR2016/052837; 5 pgs.

(Continued)

*Primary Examiner* — Simon King
(74) *Attorney, Agent, or Firm* — Maier & Maier, PLLC

(57) ABSTRACT

A multi-glazed window formed by a frame produced from profiles supporting at least two glass panes separated by an air layer. The window incorporating an active noise reduction device for a noise coming from a noise source. At least one loudspeaker an actuator associated with the membrane, which actuator is capable of inducing a vibratory movement of said membrane, at least one control microphone carried by the frame, said microphone being installed in the air layer in order to sense the acoustic signals in said air layer, and a control electronics suitable for controlling the actuator according to the acoustic signals sensed by the control microphone.

13 Claims, 6 Drawing Sheets

(51) Int. Cl.
*H03B 29/00* (2006.01)
*E06B 3/67* (2006.01)
*G10K 11/178* (2006.01)
*H04R 1/08* (2006.01)

(52) U.S. Cl.
CPC ................ *G10K 2210/3026* (2013.01); *G10K 2210/3027* (2013.01); *G10K 2210/3219* (2013.01)

(56) References Cited

OTHER PUBLICATIONS

International Search Report dated Feb. 16, 2017 of corresponding International application No. PCT/FR2016/052837; 5 pgs.

* cited by examiner (A-A)

MULTI-GLAZED WINDOW INCORPORATING AN ACTIVE NOISE REDUCTION DEVICE

FIELD

The invention has for object a multi-glazed window incorporating an active noise reduction device.

It relates to the technical field of devices that make it possible to improve the sound insulation of a window.

BACKGROUND

Document U.S. Pat. No. 6,285,773 (Carme) discloses an active noise rejection system, comprising one or several linear loudspeakers arranged at the edge of a double glazing, in the air layer between the two glass panes and/or inside a framing profile of this double glazing. In this noise rejection system, the loudspeaker makes it possible to realize an electro-acoustic system that is practically invisible, and which is not detrimental to visual comfort or to the light transmission of the glazing, with the proposed system making it possible to improve the sound insulation of a double glazing in particular in the low frequencies.

The loudspeaker described in the Carme patent, comprises a vibrating membrane disposed between two adjacent glass panes in such a way as to vibrate and generate a counter-noise in the air layer. This membrane is associated with an actuator suitable for inducing a vibratory movement to said membrane. A control electronics makes it possible to control the actuator according to the acoustic signals sensed by at least one control microphone carried by the frame of the window. The Carme patent does not focus however on the position that the control microphone has to have in order to optimize the filtration of the noise.

Patent document EP 0.710.946 (CENTRE SCIENTIFIQUE ET TECHNIQUE DU BATIMENT) also relates to a multi-glazed window incorporating an active noise reduction device. In this document, it is taught to position control microphones in the middle of the air layer, at equal distances from the two glass panes, in the longitudinal median plane of the window. The results obtained in terms of noise attenuation are however not optimal. Furthermore, the attenuation is effective only in a narrow frequency band corresponding to the low frequencies.

Patent document CN 201.620.733 (XINMIN) also discloses an active noise reduction system comprising a loudspeaker arranged in a triple glazing, in the air layer separating two glass panes. The loudspeaker and the control microphone are in the same plane.

The invention aims to overcome this situation. In particular, an objective of the invention is to improve the attenuation of the noise in a multi-glazed window of the type known from prior art mentioned hereinabove.

Another objective of the invention is to obtain an attenuation of the noise in a wide frequency band.

SUMMARY

The solution proposed by the invention is a multi-glazed window formed by a frame produced from profiles supporting at least two glass panes separated by an air layer, said window having a longitudinal median plane and incorporating an active noise reduction device for a noise coming from a noise source, which device comprises:

at least one loudspeaker which is in the form of a hollow body in the form of an elongated rectangle parallelepiped and one face of which is constituted at least partially by a vibrating membrane arranged between the two adjacent glass panes in such a way as to vibrate and generate a counter-noise in the air layer, an actuator associated with the membrane, which actuator is capable of inducing a vibratory movement of said membrane, at least one control microphone carried by the frame, said microphone being installed in the air layer in order to sense the acoustic signals in said air layer, a control electronics suitable for controlling the actuator according to the acoustic signals sensed by the control microphone.

This window is remarkable in that:

the hollow body forms one of the profiles of the frame, the membrane is arranged in the middle of the two glass panes, symmetrically with respect to the longitudinal median plane of the window, the control microphone is offset from the longitudinal median plane of the window in such a way that it is closer to the glass pane which is the farthest from the noise source than the other glass pane.

Thanks to this position of the control microphone, the applicant was able to surprisingly observe that the attenuation of the noise was effective and stable, in a frequency band larger than that indicated in patent document EP 0.710.946 mentioned hereinabove.

Other advantageous characteristics of the invention are listed hereinbelow. Each one of these characteristics can be considered alone or in combination with the remarkable characteristics defined hereinabove, and be the object, where applicable, of one or several divisional patent applications:

The control microphone can be installed on the profile formed by the hollow body of the loudspeaker, said control microphone being adjacent to the membrane.

In an alternative embodiment, the control microphone is installed on a profile which is distant from the profile formed by the hollow body of the loudspeaker.

The control microphone is advantageously oriented in a direction which is perpendicular to the direction of propagation, in the air layer, of the acoustic signals coming from the noise source.

The control electronics advantageously comprises a means of filtering by feedback having an input connected to the control microphone and an output connected to the actuator.

Preferably, at least one reference microphone is carried by the frame, which reference microphone is installed inside the air layer, at the glass pane that is the closest to the noise source; the control electronics comprises in this case a means of filtering by feedforward, having an input connected to the reference microphone and an output connected to the actuator.

The control microphone and the reference microphone can be carried by the same profile or each carried by a separate profile.

The reference microphone is advantageously oriented in a direction which is parallel to the direction of propagation of the acoustic signals coming from the noise source.

Preferably, the control electronics comprises a summing means having a first input, a second input and an output connected to the actuator; the means of filtering via feedback comprises an input connected to the control microphone and an output connected to the first input of the summing means; and the means of filtering via feedforward comprises an input connected to the reference microphone and an output connected to the second input of the summing means.

The means of filtering by feedforward can be of the adaptive type and include: —a first input connected to the control microphone; and a second input connected to the reference microphone.

The means of filtering by feedforward can also be of the non-adaptive type.

The loudspeaker can be a linear loudspeaker or a circular loudspeaker.

BRIEF DESCRIPTION OF THE DRAWINGS

Other advantages and characteristics of the invention shall appear when reading the following description of a preferred embodiment, in reference to the annexed drawings, realized by way of indicative and non-limiting examples and wherein.

DETAILED DESCRIPTION

This invention relates to a multi-glazed window, which is characterized by a particular design of the active noise reduction device that it incorporates.

Figure 1:
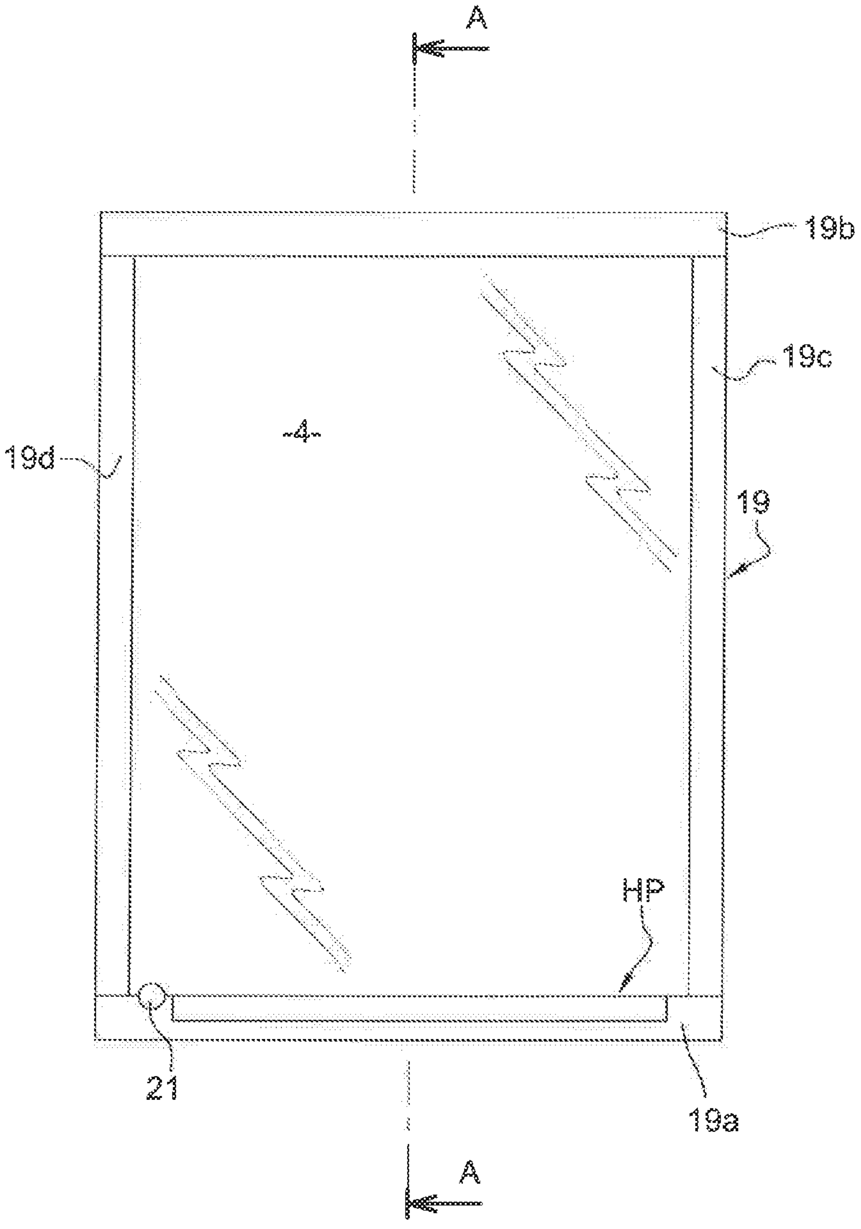
FIG. 1 is a diagrammatical front view of a multi-glazed window with an active noise reduction system comprising a linear loudspeaker.
Figure 2:
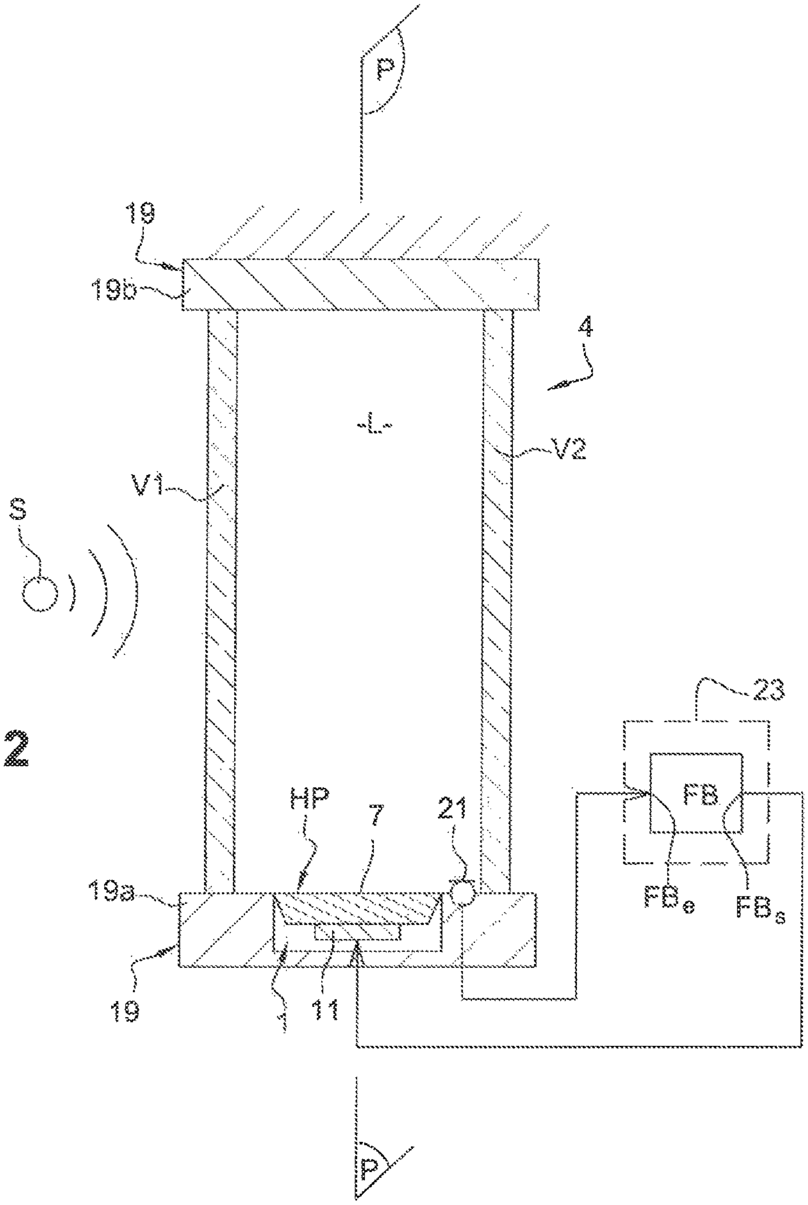
FIG. 2 is a diagrammatical view as a cross-section according to A-A of the window of FIG. 1, according to a first embodiment.

The window itself is of a known type. In FIG. 1, it is comprised of a frame 19, formed of profiles 19*a*, 19*b*, 19*c*, 19*d* surrounding a glass panel 4. The frame 19 is preferably of rectangular or square shape, but can be polygonal, have one or several curved edges, etc. In FIG. 2, the panel 4 is formed by two adjacent glass panes V1 and V2 separated by an air layer L.

The noise reduction device is used for an active control of the noise. It generates in the air layer a sound level equivalent to the ambient sound level to be controlled, in particular a noise coming from a noise source S.

An active noise reduction device can have the form of a piezoelectric actuator or a loudspeaker. Preferably use is made of a linear loudspeaker of the type described in U.S. Pat. No. 6,285,773 (Carme) mentioned hereinabove, and to which those skilled in the art can refer where applicable. This type of linear loudspeaker can indeed be housed easily in a reduced volume and in particular in a narrow space, while still having an output comparable to that of a conventional loudspeaker with conical membranes. The geometrical shape and the particular arrangement of the elements that comprise the linear loudspeaker offer a very satisfactory output. In particular, in light of the substantial length of the membrane, the latter displaces a large mass of air during its vibration, which allows for good output in the low frequencies. The linear loudspeaker furthermore makes it possible to generate a sound wave of which the phase is homogeneous over the entire width of the glazing.

Figure 6:
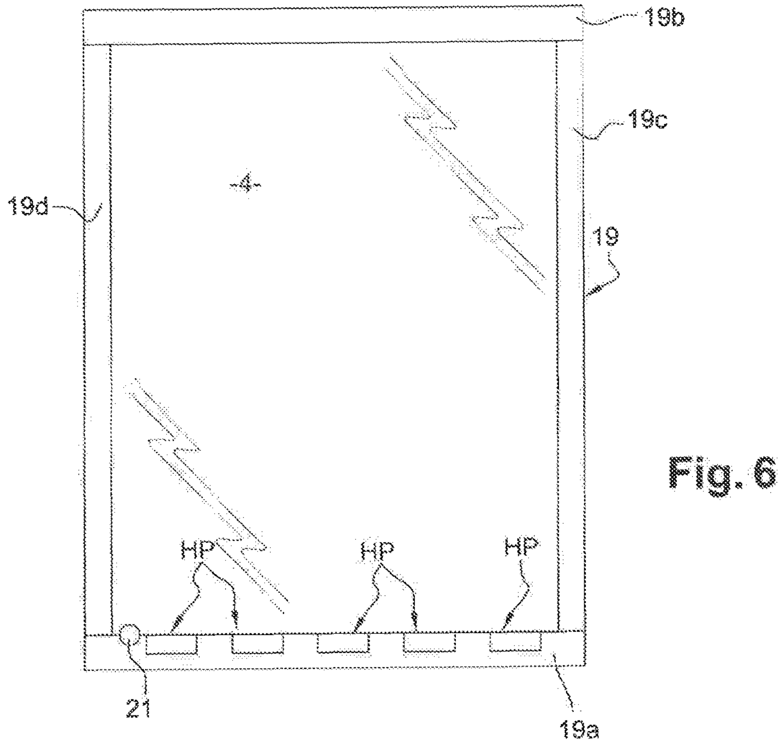
FIG. 6 is a diagrammatical front view of a multi-glazed window with an active noise reduction system comprising several circular loudspeakers.

FIG. 6 shows an alternative embodiment not covered by the invention wherein the linear loudspeaker is replaced with several circular loudspeakers installed side-by-side in the profile 19*a*. It is possible for example to use ASCA loudspeakers marketed by the applicant. The use of a linear loudspeaker makes it possible to reduce the number of loudspeakers in order to obtain an equivalent noise reduction.

Use will be made in the rest of the description of the generic term loudspeaker, whether the latter is a loudspeaker as such or a piezoelectric actuator.

The noise reduction device can include a single linear loudspeaker HP arranged on a single of the sides 19*a* of the frame 19, or several loudspeakers arranged respectively on the various sides 19*a*, 19*b*, 19*c*, 19*d* of said frame. The choice of the number of loudspeakers HP and of their arrangement in the frame 19 depends on the sound field to be attenuated, by superposition, with noises propagating in the air layer L, in order to increase the sound insulation of the double glazing.

FIG. 2 diagrammatically shows a linear loudspeaker, which exteriorly has the form of a hollow body 1 in the form of an elongated rectangle parallelepiped, having for example a length from 50 cm to 2 m, a width from 2 cm to 4 cm and a depth from 2 cm to 4 cm. The body 1 can be made from aluminum, steel, plastic, or of any other material that suits those skilled in the art and advantageously forms one of the profiles of the frame 19. In FIG. 2, the body 1 forms the horizontal profile 19*a* which is located at the bottom of the frame 19.

At least one face of the loudspeaker HP is constituted at least partially by a vibrating membrane 7 arranged between the two adjacent glass panes V1, V2 in such a way as to vibrate and generate a counter-noise in the air layer L. This membrane 7 is flat and for the case of a linear loudspeaker, it is extended. It preferably extends over the entire length of the body 1. The membrane 7 is arranged in the middle of the two glass panes V1, V2 symmetrically with respect to the longitudinal median plane P of the window.

An actuator 11 is associated with the membrane 7. This actuator 11 is adapted for inducing a vibratory movement to the membrane 7. It can be a piezoelectric actuator or more conventionally an actuator using an arrangement of magnets and a coil electrically excited to cause the vibration of the membrane 7 which generates the counter-noise.

At least one control microphone 21, or error microphone, is carried by the frame 19. In FIG. 2, this microphone 21 is installed in the air layer L in order to sense the acoustic signals propagating in the latter. By way of example it is possible to use a control microphone 21 of the PUI Audio brand bearing the reference POM-2246L-C33-Ret manufactured by the company PUI Audio.

The microphone 21 sends a signal that represents the noise in the air layer L to a control electronics 23. Then, the control electronics 23 emits a control signal to the actuator 11 according to the acoustic signals sensed by the microphone 21. This active noise reduction device makes it possible to increase the sound insulation of the double glazing.

In accordance with the invention, and as shown in FIG. 2, the control microphone 21 is installed in the air layer L, offset from the longitudinal median plane P, in such way that it is closer to the glass pane V2 which is the farthest away from the noise source S than the other glass pane V1. For example if the noise source S is the ambient noise present outside a room, a premises or a cab, (for example the noise of vehicles circulating in a street or on a road, the noise of an aircraft engine, . . . ), the glass pane V1 is that which is located outside the room, premises or cab, and the glass pane V2 is that which is installed inside the room, premises or cab. If the noise source S is the ambient noise present inside a room, premises or cab (for example the music from a discotheque), the glass pane V1 is that which is located inside the room, premises or cab, and the glass pane V2 is that which is installed outside the room, premises or cab.

Thanks to this position of the control microphone 21, the applicant was able to surprisingly observe that the attenuation of the noise was effective and stable, in a frequency band that is larger than that indicated in patent document EP 0.710.946 mentioned hereinabove. This phenomenon is explained hereinafter in reference to FIG. 7.

Good results are obtained when the control microphone 21 is oriented in a direction that is perpendicular to the direction of propagation, in the air layer L, of the acoustic signals coming from the noise source S. The control microphone 21 is as such oriented a direction which is parallel to the direction of displacement of the membrane 7, i.e. parallel to the longitudinal median plane P of the window. In this arrangement, it appears that the control microphone 21 collects in a satisfactory manner the residual acoustic signal which is used as an error signal in the filtering by feedback described hereinafter in the description. This residual acoustic signal is a combination of the residual noise reaching the glass pane V2 and of a counter-noise generated by the loudspeaker HP which is ideally the inverted copy of the noise to be suppressed coming from the source S.

In FIG. 2, the control microphone 21 is installed on the profile 19*a* formed by the hollow body 1 of the loudspeaker HP. More particularly, the control microphone 21 is adjacent to the membrane 7. This configuration simplifies the design of the active noise reduction device in that all of the elements that it is comprised of are grouped together into a single profile 19*a*.

Figure 3:
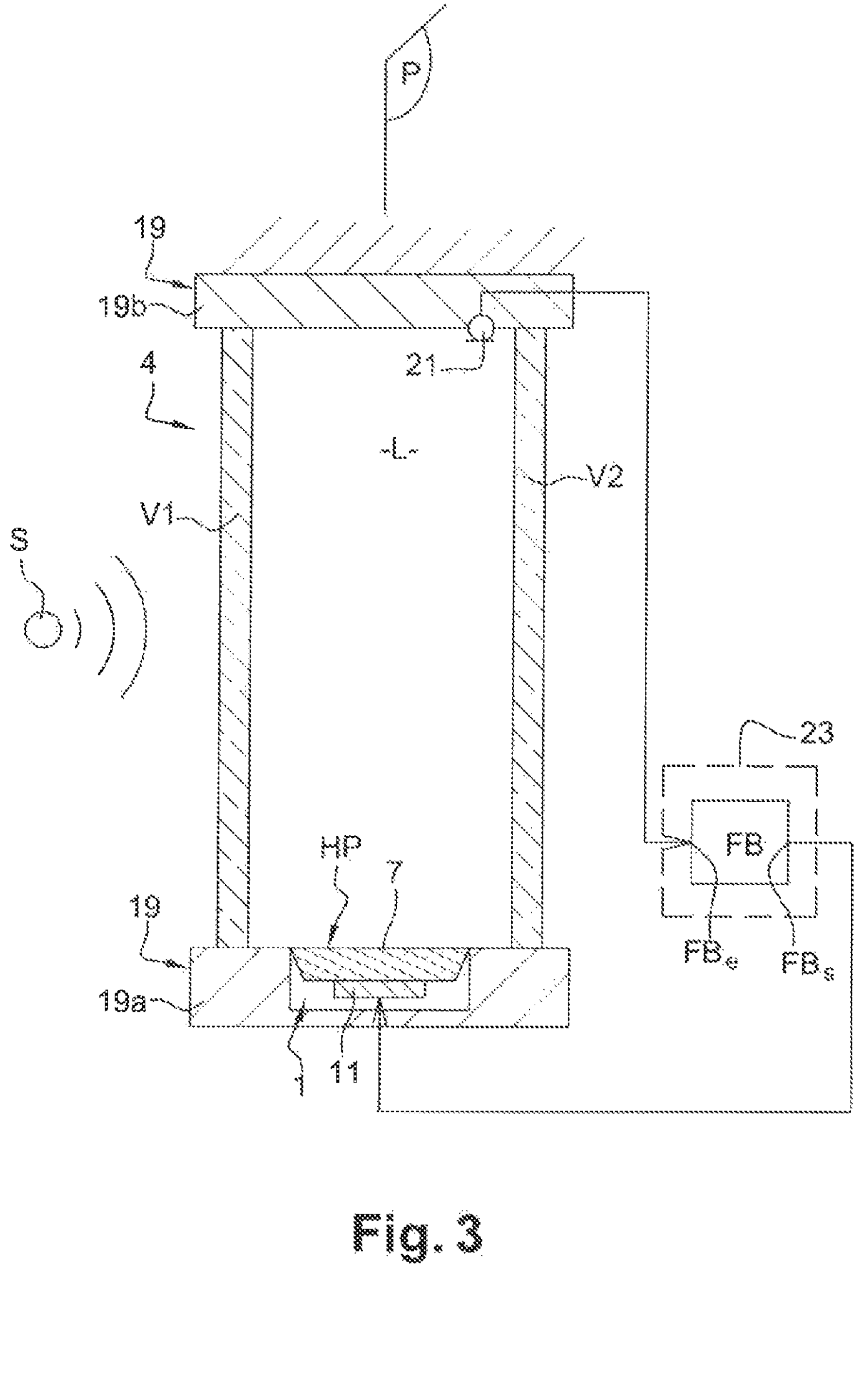
FIG. 3 is a diagrammatical view as a cross-section according to A-A of the window of FIG. 1, according to a second embodiment.

The control microphone 21 can however be installed on a profile 19*b* which is distant from the profile 19*a* formed by the hollow body 1 of the loudspeaker HP, such as is diagrammed in FIG. 3. In this figure, the control microphone 21 is arranged on a horizontal profile 19*b* which is opposite the horizontal profile 19*a* formed by the hollow body 1 of the loudspeaker HP. Of course, the control microphone 21 can be installed on one of the vertical profiles 19*c* or 19*d*, while the hollow body 1 of the loudspeaker HP forms one of the horizontal profiles 19*a* or 19*b*, and inversely.

In FIGS. 2 and 3, the control electronics 23 comprises a means of filtering via feedback FB of the non-adaptive type having an input FBe connected to the control microphone 21 and an output FBs connected to the actuator 11.

The technique of active attenuation by feedback is based on a counter-reaction loop arranged to generate an active attenuation of the sound waves propagating in the air layer L. The signal measured by the control microphone 21 is injected at the actuator 11 through the means of filtering via feedback FB which corrects said signal in order to attempt to cancel its energy. This feedback technique makes it possible to obtain an acoustic attenuation with a certain gain, without generating any instability in a treatment frequency band. Most often, this treatment frequency band corresponds to low frequencies, for example to sound waves at the frequency band ranging from 0 to 400 Hz and more particularly from 70 Hz to 400 Hz.

The control electronics 23 advantageously comprises: —preamplification means comprising an input connected to the control microphone 21 and an output connected to the input FBe of the means of filtering by feedback FB; —and amplification means comprising an input connected to the output FBs of the means of filtering by feedback FB, and an output connected to the actuator 11.

This control electronics 23 constitutes here a counter-reaction loop arranged to generate an active sound attenuation without generating any instability in a chosen frequency band. For example, the frequency band wherein the means of filtering via feedback is effective without generating any instability in Nyquist terms, is about from 0 to 600 Hz for sound waves and more particularly from 70 Hz to 600 Hz.

In practice, the means of filtering via feedback FB comprises a plurality of active analog filters of a magnitude greater than or equal to 1, arranged in order to generate a transfer function making it possible to prevent instabilities in the frequency band 0-600 Hz and more particularly in the band 70-600 Hz in Nyquist terms, and the transfer function of the means of filtering FB is determined in such a way that the phase of said transfer function does not pass through the value 0 in this band.

However, a pumping effect appears beyond 600 Hz which results in an increase in the level of noise in relation to the action of the passive means of attenuation alone, i.e. the panel 4 alone. This phenomenon is entirely known to those skilled in the art, and forms a non-linearity (degradations in performance) in relation to the expected results of the observation of the system in an open loop.

Figure 4:
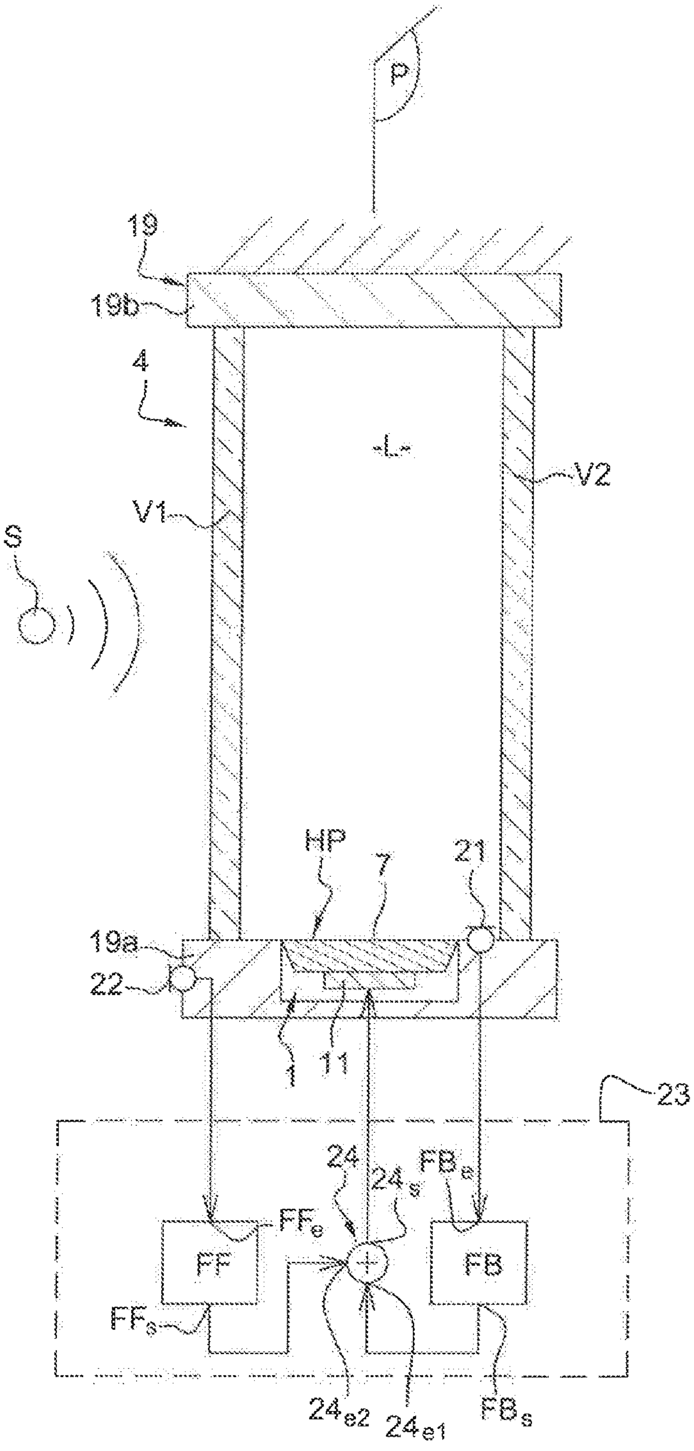
FIG. 4 is a diagrammatical view as a cross-section according to A-A of the window of FIG. 1, according to a third embodiment.

In order to overcome this, it is advantageous to combine the active attenuation by feedback with an active attenuation by feedforward. In FIG. 4, the control electronics 23 comprises for this purpose a means of filtering by feedforward FF, having an input FFe connected to a reference microphone 22 and an output FFs connected to the actuator 11.

By way of example it is possible to use a reference microphone 22 of the PUI Audio brand bearing the reference POM-2246L-C33-Ret manufactured by the company PUI Audio.

In this technique of active attenuation by feedforward, a reference acoustic field, upstream of the propagation of the acoustic field in the air layer L, is detected by the reference microphone 22, the treated by the means of filtering FF in order to determine the control to be applied to the actuator 11.

In order to optimize the treatment of the signals, the following provided: —preamplification means comprising an input connected to the reference microphone 22 and an output connected to the input FFe of the means of filtering by feedforward FF; —and amplification means comprising an input connected to the output FFs of the means of filtering by feedforward FF, and an output connected to the actuator 11.

In FIG. 4, the control electronics 23 comprises a summing means 24 having: —a first input 24*e*1 connected to the output FBs of the means of filtering by feedback FB; —a second input 24*e*2 connected to the output FFs of the means of filtering by feedforward FF; —and an output 24*s* connected to the actuator 11. The output signal of the summing means 24 which is applied to the actuator 11 is as such a linear combination of the signals coming from the routes of filtering by feedback and by feedforward. Amplification means are advantageously provided comprising an input connected to the output 24*s* of the summing means 24, and an output connected to the actuator 11.

The technique by feedforward is articulated around the means of filtering by feedforward FF of the adaptive or non-adaptive type. Compared to a non-adaptive filtering, the adaptive filtering is more effective from a noise attenuation standpoint, but requires more substantial calculating power and a higher cost for realization.

In the case where the means of filtering via feedforward FF is of the non-adaptive type, the transfer function thereof is a fixed function that is preset and which does not vary.

With an adaptive means of filtering by feedforward FF, the transfer function is modified dynamically, continuously, by a real-time analysis algorithm of the acoustic signal coming from the source S. The coefficients of the means of filtering by feedforward FF are adapted in real time according to an algorithm chosen in such a way as to minimize the energy of the vibrations sensed by the control microphone 21 according to the energy of the reference vibrations sensed by the reference microphone 22.

Figure 5:
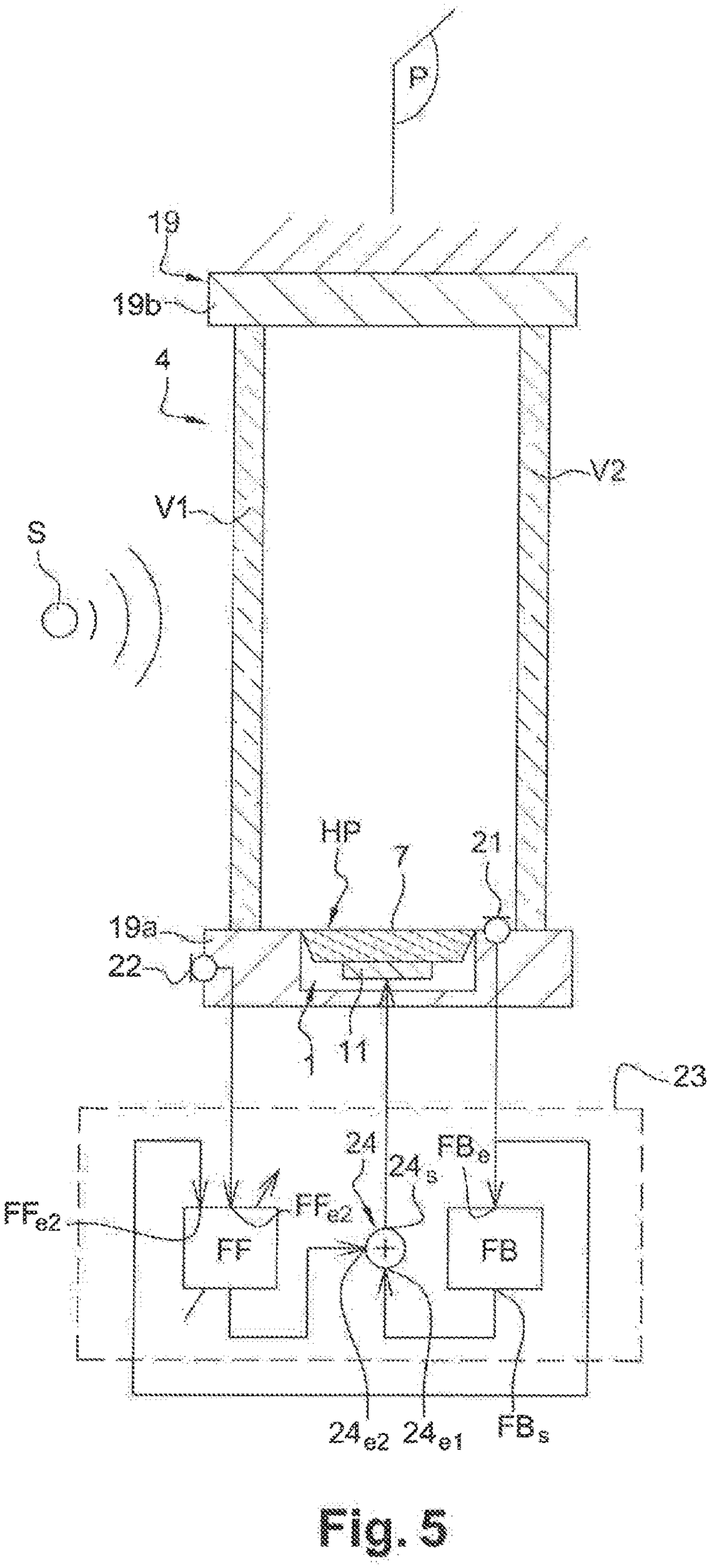
FIG. 5 is a diagrammatical view as a cross-section according to A-A of the window of FIG. 1, according to a fourth embodiment.

This adaptive filtering is diagrammed in FIG. 5 wherein the means of filtering via feedforward FF comprises: a first input FFe1 connected to the control microphone 21; and a second input FFe2 connected to the reference microphone 22. In practice, the means of filtering via feedforward FF comprises finite pulse response filters of the adaptive type. The coefficients of these filters are updated in real time by a minimization algorithm which takes account the signals sensed by the control microphone 21. For example, the minimization algorithm is of the least mean squares type (LMS) or more advantageously of the filtered-X least mean squares type (FXLMS).

In a prior step of initialization, the transfer function of the so-called secondary path between the loudspeaker HP and the control microphone 21 is measured, sampled, and saved in the memory of a processor of the control electronics 23. This transfer function measured as such beforehand will then be used in the calibration phase for the adaptation of the filtering elements by feedforward. This step is carried out in a manner known to those skilled in the art.

The active attenuation of the "hybrid" type obtained according to the invention is the result of a combination of the means of filtering by feedforward and by feedback wherein the filtering by feedforward is grafted onto the filtering by feedback or reciprocally. This makes it possible to linearize the feedback attenuation in all of a frequency band that is wider than the frequency band (0-600 Hz and more particularly 70-600 Hz) treated directly by the means of filtering via feedback FB, to accelerate the convergence of the minimization algorithm, and to improve the robustness of the means of filtering by feedforward FF. As such the gain in attenuation is improved in a widened band which can range up to 4000 Hz, by suppression of the pumping effect mentioned hereinabove.

In FIGS. 4 and 5, the reference microphone 22 is carried by the frame 19. Contrary to the control microphone 21, it is installed inside the air layer L, at the glass pane V1 that is the closest to the noise source S. The reference microphone 22 can as such optimally sense the copy of the noise to be suppressed coming from the source S and transmit this signal to the control electronics 23.

Good results are obtained when the reference microphone 22 is oriented in a direction that is parallel to the direction of propagation of the acoustic signals coming from the noise source S. The reference microphone 22 is as such oriented in a direction which is perpendicular to the direction of displacement of the membrane 7, i.e. perpendicular to the longitudinal median plane P of the window. In this arrangement, it appears that the reference microphone 22 collects in a satisfactory manner the acoustic signal coming from the noise source S, without being disturbed by the counter-noise generated by the loudspeaker HP.

In order to simplify the design of the noise reduction device, the reference microphone 22 and the control microphone 21 are carried by the same profile 19*a*. It can however be provided that the control microphone 21 and the reference microphone 22 are each carried by a separate profile. The reference microphone 22 can for example be arranged on a horizontal profile 19*b* which is opposite the horizontal profile 19*a* formed by the hollow body 1 of the loudspeaker HP and the control microphone 21. It can also be installed on one of the vertical profiles 19*c* or 19*d*, while the loudspeaker HP and the control microphone 21 are installed on one of the horizontal profiles 19*a* or 19*b*, and inversely.

Figure 7:
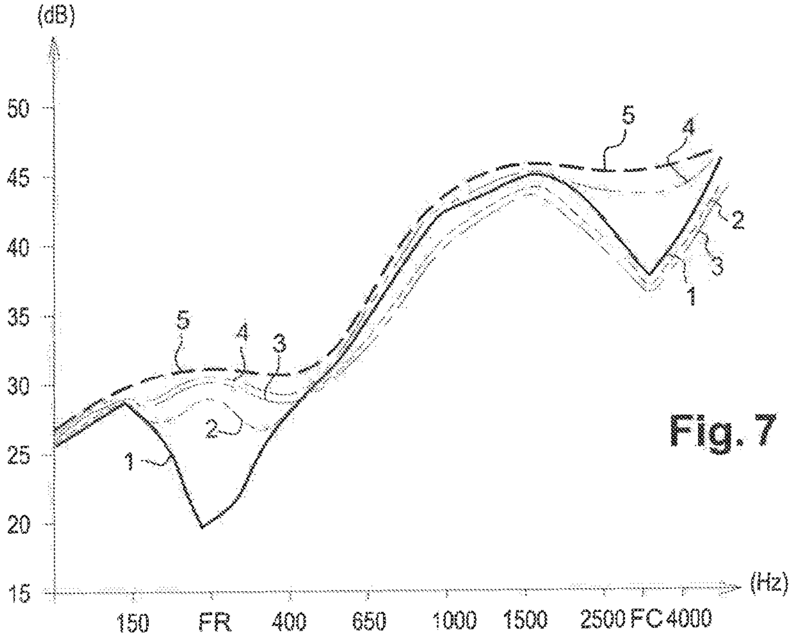
FIG. 7 is a graph showing the acoustic attenuation that can be procured by a window in accordance with the invention.

FIG. 7 is a graph showing the acoustic attenuation that can be procured by a window in accordance with the invention. The measurements were taken on a double glazing window of the 4-12-4 type (glass pane; air layer; thickness of the glass=4 mm; thickness of the air layer=12 mm). The curves corresponding to the acoustic attenuation values in dB (ordinates) according to the frequency in Hz (abscissa). The table 1 hereinbelow shows the various cases.

TABLE 1

| Curve no. | Graphics representation | Cases | Type of acoustic filtration |
|---|---|---|---|
| 1 | ——————— | Double glazing alone without noise reduction device | Without acoustic filtering |
| 2 | - - - - - - - - - - - - | Double glazing with noise reduction device. Control microphone 21 installed in the middle of the air layer. No reference microphone 22. | FEEDBACK alone |
| 3 | —·—·—·—·—·— | Double glazing with noise reduction device. Control microphone 21 installed near the glass pane V2. No reference microphone 22. | FEEDBACK alone (FIG. 2) |
| 4 | —··—··—··—··— | Double glazing with noise reduction device. Control microphone 21 installed near the glass pane V2. Reference microphone 22 installed. | Non-adaptive FEEDBACK + FEEDFORWARD (FIG. 4) |
| 5 | — — — — — — — — | Double glazing with noise reduction device. Control microphone 21 installed near the glass pane V2. Reference microphone 22 installed. | Adaptive FEEDBACK + FEEDFORWARD (FIG. 5) |

By analyzing the curve no. 1, it is noted that the acoustic insulation that the double glazing procures is relatively poor. The acoustic attenuation is low in the low and medium frequencies (150 Hz to 400 Hz, corresponding for example to the noise of slow road traffic) with a maximum reduction on the resonance frequency Fr (about 250 Hz). This resonance frequency depends on the mass of the glass panes V1, V2, their thickness and the nature of the elements (materials and air layer/gas) comprising the panel 4. Beyond this resonance frequency Fr, the acoustic insulation increases linearly until the critical frequency Fc of the single glass panes V1 and V2 which comprise the panel 4 (about 3000 Hz for a glass 4 mm thick).

This can be explained by the fact that the double glazing acts as an acoustic system of the Mass/Spring/Mass type. The air layer L playing the role of a spring, its thickness is generally too low to create a sufficiently flexible spring and the system causes the glass panes V1 and V2 to resonate.

The curve no. 2 corresponds to the case wherein the double glazing incorporates the noise reduction device. Only a filtering by feedback FEEDBACK is provided. The control microphone 21 is installed in the middle of the air layer L, as is recommended by patent document EP 0.710.946 mentioned hereinabove. Note an improvement in the acoustic insulation of about 8 dB in the low frequency range close to the resonance frequency Fr, over a band of about 200 Hz-350 Hz. Also observed is a decrease in the acoustic insulation in relation to the acoustic insulation that the double glazing alone procures (pumping effect beyond 650 Hz).

The curve no. 3 corresponds to the case wherein the double glazing incorporates the noise reduction device, the control microphone 21 now being installed as close as possible to the glass pane V2 which is the farthest from the noise source S. Only a filtering by feedback FEEDBACK is provided. As on the curve no. 2, note an improvement in the acoustic insulation of about 8 dB in the range of the low frequencies close to the resonance frequency Fr. The acoustic insulation is however improved in a wider band by about 150 Hz-375 Hz.

The curve no. 4 corresponds to the case wherein the double glazing incorporates the noise reduction device. A non-adaptive filtering by feedback FEEDBACK and filtering by feedforward FEEDFORWARD are provided. The control microphone 21 is installed as close as possible to the glass pane V2. Note an improvement in the acoustic insulation of about 8 dB in the low frequency range close to the resonance frequency Fr, over a band of about 150 Hz-375 Hz (as on curve no. 3). Also observe an improvement in the acoustic insulation by about 5 dB in the high frequency range close to the critical frequency Fc, which improvement is due to the filtering by feedforward.

The curve no. 5 corresponds to the case where the double glazing incorporates the noise reduction device. An adaptive filtering by feedback FEEDBACK and a filtering by feedforward FEEDFORWARD are provided. The control microphone 21 is installed as close as possible to the glass pane V2. Note an improvement in the acoustic insulation by about 10 dB in the range of the low frequencies close to the resonance frequency Fr, over a wider band of about 125 Hz-400 Hz. Also observe an improvement in the acoustic insulation by about 8 dB in the high frequency range close to the critical frequency Fc. The attenuation is here therefore generally more effective compared to the curve 4. The combination of the adaptive filterings by feedforward and by feedback makes it possible to improve the respective behavior of said filterings.

The arrangement of the various elements and/or means of the invention, in the embodiments described hereinabove, must not be understood as requiring such an arrangement in all of the implementations. In any case, it is understood that diverse modifications can be made to these elements and/or means, without leaving the spirit and the scope of the invention. In particular:

The window can comprise more than two glass panes, in particular three glass panes.

Several control 21 or reference 22 microphones can be connected to the control electronics 23, with these microphones being preferably installed on each one of the profiles 19*a*, 19*b*, 19*c*, 19*b* of the frame 19; in this case, the control algorithm manages each path with for objective to minimize the level of pressure on each one of the error microphones, from the information collected on the multiple reference microphones.

The filter by feedback FEEDBACK can be adaptive, by using for example an algorithm of the IMC-FXLMS type pour "Internal Model Control Filtered-X Least Mean Squares".

Regarding the control algorithms in FEEDBACK and/or FEEDFORWARD mode, the treatment can be either analog or digital.

Outside the scope of this invention, the filter by feedforward FEEDFORWARD can be used alone, without a filter by feedback FEEDBACK.

The invention claimed is:

1. A multi-glazed window formed by a frame produced from profiles supporting at least two glass panes separated by an air layer, said window having a longitudinal median plane and incorporating an active noise reduction device for a noise coming from a noise source, which device comprises:

at least one loudspeaker which is in the form of a hollow body in the form of an elongated rectangle parallelepiped and one face of which is constituted at least partially by a vibrating membrane arranged between the two adjacent glass panes in such a way as to vibrate and generate a counter-noise in the air layer, an actuator associated with the membrane, which actuator is capable of inducing a vibratory movement of said membrane, at least one control microphone carried by the frame, said microphone being installed in the air layer in order to sense the acoustic signals in said air layer, a control electronics suitable for controlling the actuator according to the acoustic signals sensed by the control microphone, wherein the hollow body forms one of the profiles of the frame, the membrane is arranged in the middle of the two glass panes, symmetrically with respect to the longitudinal median plane of the window, the control microphone is offset from the longitudinal median plane of the window in such a way that it is closer to the glass pane which is the further from the noise source than the other glass pane.

2. The window according to claim 1, wherein the control microphone is installed on the profile formed by the hollow body of the loudspeaker, said control microphone being adjacent to the membrane.

3. The window according to claim 1, wherein the control microphone is installed on a profile which is distant from the profile formed by the hollow body of the loudspeaker.

4. The window according to claim 1, wherein the control microphone is oriented in a direction that is perpendicular to the direction of propagation, in the air layer, of the acoustic signals coming from the noise source.

5. The window according to claim 1, wherein the control electronics includes a means of filtering via feedback having an input connected to the control microphone and an output connected to the actuator.

6. The window according to claim 1, wherein:

at least one reference microphone is carried by the frame, which reference microphone is installed inside the air layer, at the glass pane that is the closest to the noise source, the control electronics includes a means of filtering via feedforward, having an input connected to the reference microphone and an output connected to the actuator.

7. The window according to claim 6, wherein the control microphone and the reference microphone are carried by the same profile.

8. The window according to claim 6, wherein the control microphone and the reference microphone are each carried by a separate profile.

9. The window according to claim 6, wherein the reference microphone is oriented in a direction that is parallel to the direction of propagation of the acoustic signals coming from the noise source.

10. The window according to claim 6, wherein:

the control electronics comprises a summing means having a first input, a second input and an output connected to the actuator, the means of filtering via feedback comprises an input connected to the control microphone and an output connected to the first input of the summing means, the means of filtering via feedforward comprises an input connected to the reference microphone and an output connected to the second input of the summing means.

11. The window according to claim 6, wherein the means of filtering via feedforward is of the adaptive type and comprises:

a first input connected to the control microphone, a second input connected to the reference microphone.

12. The window according to claim 6, wherein the means of filtering via feedforward is of the non-adaptive type.

13. The window according to claim 1, wherein the loudspeaker is a linear loudspeaker.

* * * * *